US00PP17106P3

(12) United States Plant Patent
Brown

(10) Patent No.: US PP17,106 P3
(45) Date of Patent: Sep. 19, 2006

(54) ***LANTANA* PLANT NAMED 'RIVRRED'**

(50) Latin Name: *Lantana camara*
Varietal Denomination: RIVRRED

(76) Inventor: Richard Brown, 11010 Riverview Dr., Riverview, FL (US) 33569

( * ) Notice: Subject to any disclaimer, the term of this patent is extended or adjusted under 35 U.S.C. 154(b) by 27 days.

(21) Appl. No.: 10/934,953

(22) Filed: Sep. 3, 2004

(65) Prior Publication Data

US 2006/0053518 P1 Mar. 9, 2006

(51) Int. Cl.
*A01H 5/00* (2006.01)

(52) U.S. Cl. ..... Plt./227

(58) Field of Classification Search ..... Plt./227
See application file for complete search history.

(56) References Cited

U.S. PATENT DOCUMENTS

PP10,854 P 4/1999 Roberson
PP14,318 P2 11/2003 Roberson

*Primary Examiner*—Kent Bell
(74) *Attorney, Agent, or Firm*—Knobbe, Martens, Olson & Bear, LLP

(57) ABSTRACT

A new and distinct *Lantana* plant cultivar is disclosed, characterized by inflorescence umbels with Red/Orange flower color. The plants have increased inflorescence longevity, compact size, and a mounding, uniformly round plant shape.

1 Drawing Sheet

Figure 1:
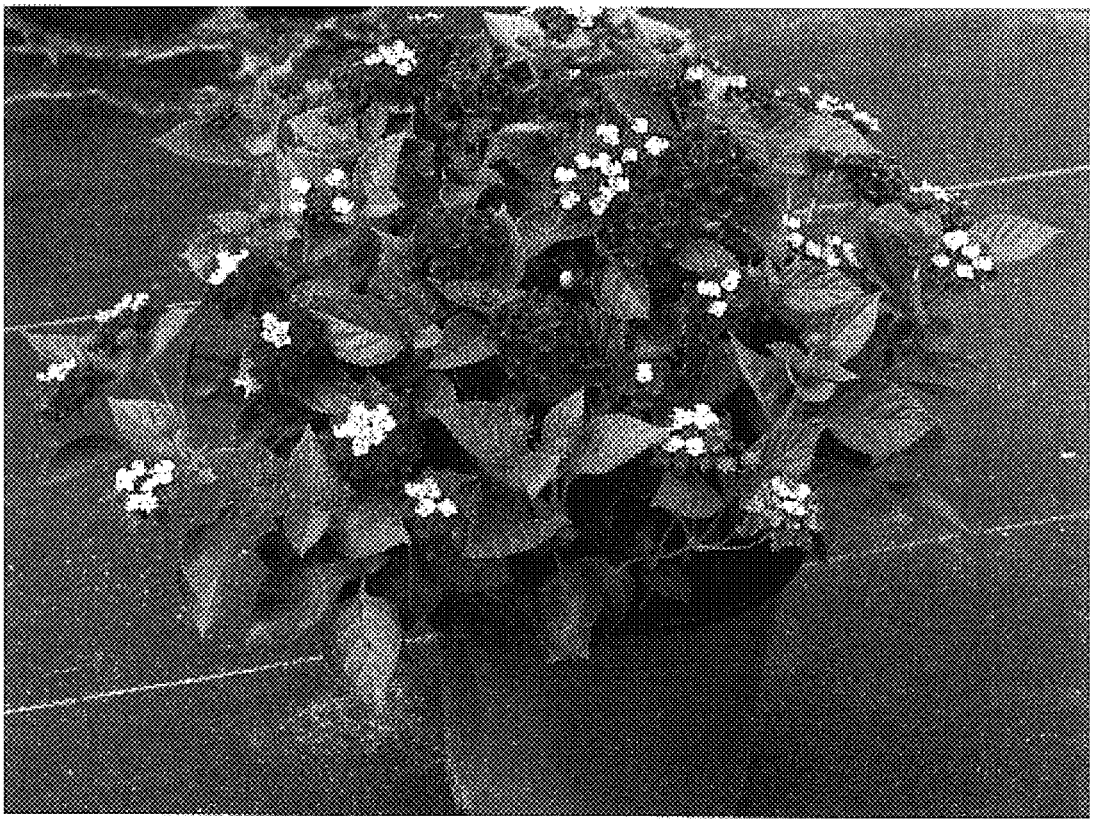

Latin name of the genus and species: *Lantana camara.*
Variety denomination: 'RIVRRED'.

BACKGROUND OF THE INVENTION

The new cultivar is a product of hybridization of an unknown female parent *Lantana* variety and an unknown male parent *Lantana camara* variety. To prepare for the hybridization, the inventor collected 16 different *lantana* varieties having red coloration in the flowers. These varieties were placed together away from other blooming *lantana* plants in March through July of 2001, in order to promote red dominance in the resulting seedlings. The seeds were gathered and planted. In September, 2001, the resulting seedlings flowered. The new cultivar 'RIVRRED' was discovered as a single plant growing among the flowering seedlings and selected by the inventor in September, 2001.

Asexual reproduction of the new cultivar by terminal tip cuttings was performed in a controlled environment in Riverview, Fla., and in Oxnard, Calif., and has shown that the unique features of this cultivar are stable and reproduced true to type on successive generations.

SUMMARY OF THE INVENTION

The *Lantana* cultivar 'RIVRRED' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'RIVRRED'. These characteristics in combination distinguish 'RIVRRED' as a new and distinct *Lantana* cultivar:

1. Red/Orange flower color.
2. Mounding, very uniformly round plants.
3. More compact form than comparable varieties.

4. Longer inflorescence (umbel) longevity than comparable varieties.

In comparison to the commercially available variety 'ROBMORNORG' (U.S. Plant Pat. No. 14,318), the new variety 'RIVRRED' has a larger diameter inflorescence than the inflorescence of 'ROBMORNORG.' Additionally, the longevity of the inflorescence (umbel) of the new variety 'RIVRRED' is approximately 3–4 days longer than the inflorescence longevity of 'ROBMORNORG.' Further, the new variety has a much rounder and compact plant form than the comparable variety 'ROBMORNORG.'

In comparison to the commercially available variety 'ROBPATCHE' (U.S. Plant Pat. No. 10,854), the new variety 'RIVRRED' has a smaller diameter inflorescence, and has slightly less florets per umbel than the comparable variety 'ROBPATCHE.' Further, the new variety 'RIVRRED' is more compact than the comparable variety 'ROBPATCHE.' Additionally, the new variety has a more round and mounding plant form in comparison to 'ROBPATCHE.'

BRIEF DESCRIPTION OF THE PHOTOGRAPH

The accompanying photograph in FIG. 1 illustrates in full color a typical plant of 'RIVRRED' grown in a 1 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements were performed in Riverview, Fla. during the month of September, 2003. The observed 'RIVRRED' plants were 49 days old, and were grown outdoors from rooted terminal tip cuttings.

The growing temperature ranged from about 15° C. to 30° C. at night to about 20° C. to 33° C. during the day. Measurements and numerical values represent averages of typical flowering types, and are believed to apply to plants of the variety grown under similar conditions of soil and climate elsewhere:

PROPAGATION

Time to initiate roots: About 14 days to initiate rooting at 24 to 30° C.
Time to develop roots: About 25 days to develop roots at 24 to 30° C.
Root description: Fine, Fibrous.

PLANT

Growth habit: Mounding perennial shrub.
Height: About 22 cm.
Plant spread: About 28 cm.
Growth rate: Rapid.
Lateral branches:
*Branching characteristics.*—Free Branching.
*Number of leaves per lateral branch.*—About 18.
*Lateral branch length.*—About 17 cm.
*Branch color.*—Near Yellow-green 145A.
*Branch diameter.*—About 0.4 cm.
*Internode length* (*at middle of stem*).—About 1.8 cm.
*Branch strength.*—Soft to moderate.

FOLIAGE

Leaf:
*Arrangement.*—Opposite, single.
*Average length.*—About 6.4 cm.
*Average width.*—About 4.8 cm.
*Shape of blade.*—Ovate.
*Apex.*—Acute.
*Base.*—Obtuse.
*Attachment.*—Stalked.
*Margin.*—Serrate.
*Texture of top surface.*—Pubescent.
*Texture of bottom surface.*—Pubescent.
*Color.*—Young foliage upper side: Near Green 137D. Young foliage under side: Near Green 138B. Mature foliage upper side: Near qreen 137C. Mature foliage under side: Near Green 137D. Venation upper side: Near Yellow-green 146D. Venation under side: Near Yellow-green 146D. Venation type: Pinnate. Leaf persistence: Persistent.
Petiole:
*Average length.*—About 1.8 cm.
*Color.*—Near Yellow-green 146D.
*Diameter.*—About 0.3 cm.
*Surface texture.*—Pubescent.

BLOOM

Flower bud:
*Length.*—About 0.2 cm.
*Diameter.*—About 0.2 cm.
*Form.*—Globular.
*Color.*—Near Yellow 9D.
Peduncle:
*Length.*—About 4.2 cm.
*Angle to stem.*—About 30°.
*Strength.*—Strong and flexible.
*Color.*—Near Yellow-green 146C.
*Diameter.*—About 0.3 cm.
Sepals:
*Appearance.*—Matte.
*Texture.*—Pubescent.
*Number.*—5 fused sepals per flower (floret).
*Shape.*—Linear.
*Margin.*—Entire.
*Apex.*—Acute.
*Length.*—About 0.3 cm.
*Width.*—About 0.1 cm.
*Color.*—Upper side: Near Yellow-green 146C. Under side: Near Yellow-green 146C.
Pedicels:
*Length.*—Less than 0.1 cm.
*Diameter.*—Less than 0.1 cm.
*Texture.*—Smooth.
*Color.*—Near Yellow-green 145A.
Inflorescence:
*Inflorescence form.*—Salverform flowers arranged in axillary umbels, flowers facing upward.
*Natural flowering season.*—Flowering continuously from Spring until temperatures near 0° C.
*Lastingness of inflorescence* (*umbel*).—Approximately 30 days.
*Number of flowers per umbel.*—About 22.
*Flower fragrance.*—Moderate, spicy.
*Inflorescence diameter.*—About 4.1 cm.
*Flower diameter.*—About 1 cm.
*Inflorescence depth.*—About 1.9 cm.
*Lastingness of individual flower* (*floret*) *on plant.*—About 8 days.
*Persistence.*—Self cleaning.
*Shape.*—Flared trumpet, corolla fused, four parted.
*Texture.*—Matte.
Flower color:
*Upper surface at first opening.*—Near Yellow 10D.
*Upper surface at maturity.*—Near Orange-red 33A.
*Upper surface at fading.*—Near Red 44B.
*Under surface at first opening.*—Near Yellow 10C.
*Under surface at maturity.*—Near Orange-red 33B.
*Under surface at fading.*—Near Red 44B.
*Petal arrangement.*—Single whorl of four petals.
*Petal symmetry.*—Asymmetrical, 2 petals slightly larger and of the same size. Smaller 2 petals of similar size to each other.
Larger petals:
*Length from base.*—About 0.4 cm.
*Length from throat of corolla tube.*—About 0.2 cm.
*Width.*—About 0.3 cm.
*Shape.*—Spatulate.
*Apex.*—Round.
*Base.*—Fused.
*Margin.*—Entire.
*Surface.*—Matte.
Smaller petals:
*Length from base.*—About 0.3 cm.
*Length from throat of corolla tube.*—About 0.1 cm.
*Width.*—About 0.2 cm.
*Shape.*—Orbicular.
*Apex.*—Round.
*Base.*—Fused.
*Margin.*—Entire.
*Surface.*—Matte.
Corolla tube:
*Corolla tube length.*—About 0.7 cm.
*Corolla tube diameter at opening.*—About 0.6 cm.
*Corolla tube diameter at base.*—About 0.1 cm.

*Pubescence of outer surface.*—Very lightly pubescent.
*Pubescence of inner surface.*—Very lightly pubescent.
*Color of outer surface.*—Near Orange-red 33B.
*Color of inner surface.*—Near Orange-red 33A.

REPRODUCTIVE ORGANS

*Number of pistils per flower.*—1.
*Pistil length.*—Less than about 0.1 cm.
*Style color.*—Near Yellow-green 154A.
*Style length.*—Less than about 0.05 cm.
*Stigma length.*—About 0.3 cm.
*Stigma shape.*—Bi-lobed.
*Stigma color.*—Near Yellow-green 154A.
*Ovary color.*—Near Yellow-green 145C.
*Number of stamens per flower.*—4.
*Anther shape.*—Oblong.
*Anther arrangement.*—Adnate to corolla tube.
*Anther color.*—Near Yellow 7A.
*Pollen color.*—Near Yellow 7A.
*Pollen quantity.*—Minimal.

Fruit:
*Fruit type.*—Berry.
*Shape.*—Globular.
*Size.*—About 0.6 cm in diameter.
*Fruit production.*—Moderate production.
*Surface.*—Smooth.
*Color of immature fruit.*—Near Yellow-green 146D.
*Color of mature fruit.*—Near Black 202A.

OTHER CHARACTERISTICS

Disease resistance: Neither resistance nor susceptibility has been observed in this variety.
Drought tolerance/cold tolerance: Neither resistance nor susceptibility has been observed in this variety.

What is claimed is:

1. A new and distinct cultivar of *Lantana* plant named 'RIVRRED' as herein illustrated and described.

* * * * *